United States Patent [19]

Wunderlich

[11] Patent Number: 4,741,331
[45] Date of Patent: May 3, 1988

[54] DISPOSABLE RADIOACTIVE AEROSOL INHALATION APPARATUS

[75] Inventor: Alan Wunderlich, Miller Place, N.Y.

[73] Assignee: Atomic Products Corporation, Shirley, N.Y.

[21] Appl. No.: 9,463

[22] Filed: Feb. 2, 1987

[51] Int. Cl.$^4$ .............................................. A61M 11/00
[52] U.S. Cl. ........................... 128/200.14; 128/200.21; 128/654
[58] Field of Search ....... 128/654, 1.1, 200.14–200.21, 128/910

[56] References Cited

U.S. PATENT DOCUMENTS

| | | | |
|---|---|---|---|
| 3,666,955 | 5/1972 | Suprenant et al. | 128/654 |
| 3,777,742 | 12/1973 | Aumiller et al. | 128/654 |
| 3,957,033 | 5/1976 | Winchell et al. | 128/654 |
| 4,116,387 | 9/1978 | Kremer, Jr. et al. | 128/200.18 X |
| 4,510,929 | 4/1985 | Bordoni et al. | 128/654 X |
| 4,598,704 | 7/1986 | Bordoni et al. | 128/200.14 |
| 4,657,007 | 4/1987 | Carlin et al. | 128/200.21 X |
| 4,660,547 | 4/1987 | Kremer, Jr. | 128/654 X |

Primary Examiner—Kyle L. Howell
Assistant Examiner—Angela D. Sykes
Attorney, Agent, or Firm—Cobrin & Godsberg

[57] ABSTRACT

Aerosol inhalation apparatus for supplying an aerosol mist containing radioactive tagged particles and air to a person, includes a nebulizer for producing the aerosol mist; a filter having one end open to atmosphere; a first conduit connecting the opposite end of the filter and the nebulizer; a second conduit having one end fluidly connected to the first conduit; a mouthpiece connected to the opposite end of the second conduit; and a reusable container for containing the nebulizer, filter and first conduit; whereby, during inhalation, the aerosol mist travels to the second conduit from the nebulizer and the first conduit, and during exhale, exhaust air and aerosol mist travel to the filter from the second conduit through the first conduit such that the exhaust air is expelled to atmosphere and the aerosol mist becomes trapped. The nebulizer includes a housing for containing radioactive solution; an aerosol device in the housing for producing the aerosol mist, the aerosol device including a mixing chamber having a small outlet opening and being used to mix the radioactive tagged particles and air to form the aerosol mist, an oxygen supply tube for supplying oxygen to the chamber, a radioactive solution supply tube for supplying the radioactive solution from the housing to the chamber in response to the oxygen supply thereto, whereby the aerosol mist exits through the small outlet opening; and a diffuser positioned immediately above the small outlet opening for breaking up radioactive tagged particles of the aerosol mist into smaller particles.

11 Claims, 3 Drawing Sheets

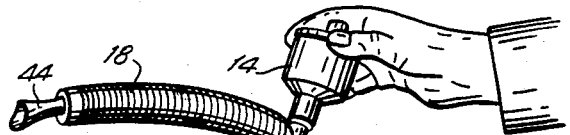
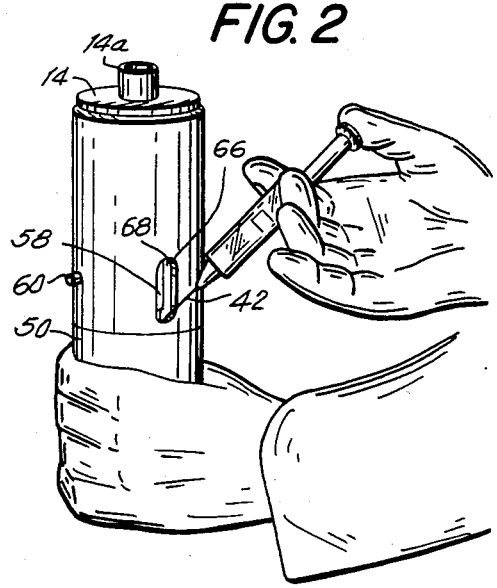
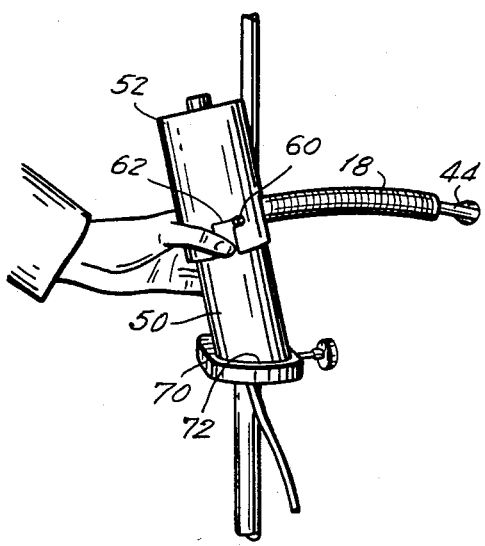
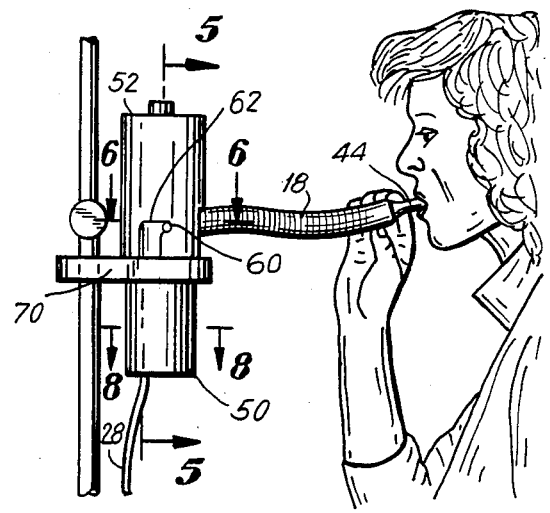

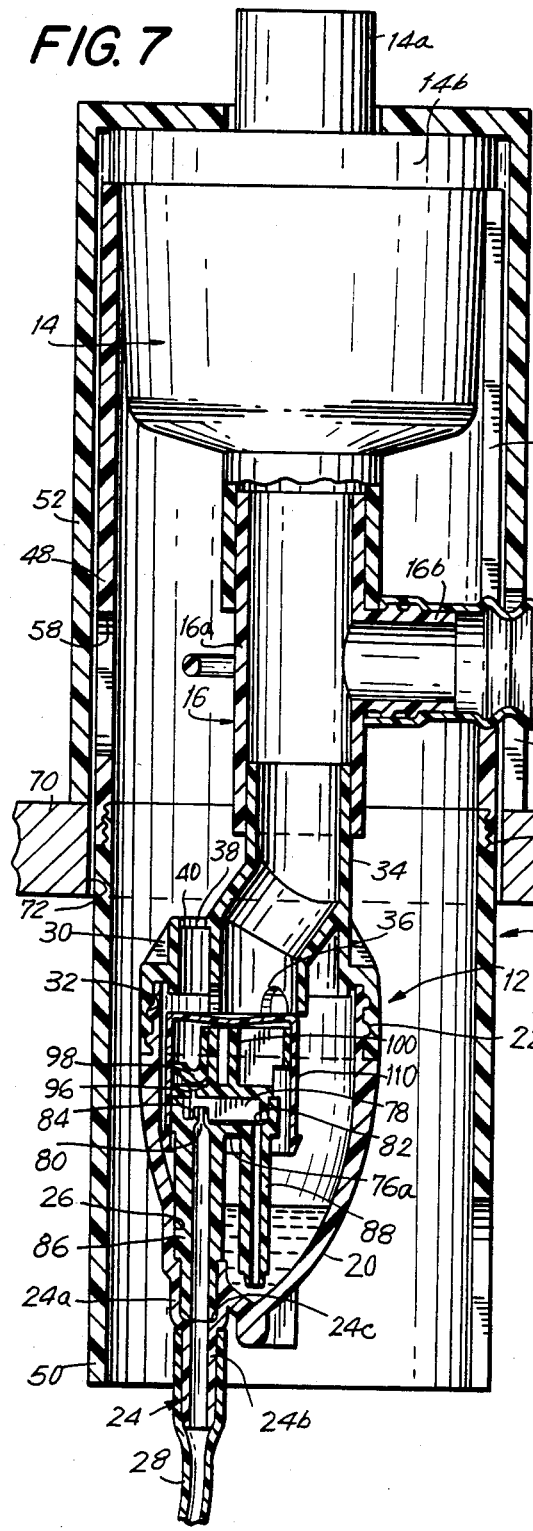
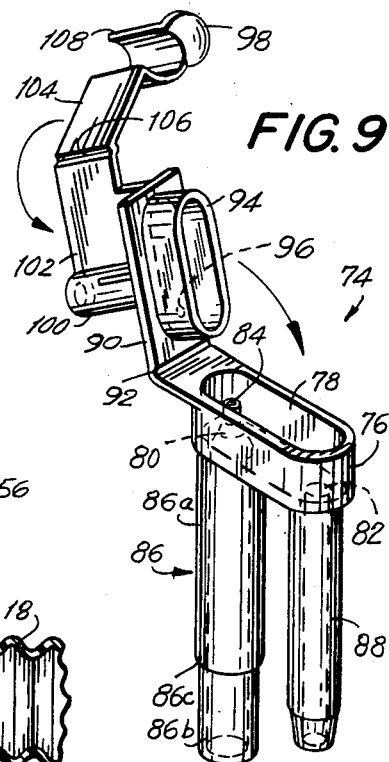
FIG. 7
FIG. 9
FIG. 8

DISPOSABLE RADIOACTIVE AEROSOL INHALATION APPARATUS

BACKGROUND OF THE INVENTION

The present invention relates generally to apparatus for diagnostic testing of a patient's pulmonary system, and more particularly, is directed to a disposable radioactive aerosol inhalation apparatus.

In order to perform ventilation scanning studies on a patient, it is necessary for the patient to inhale radioactive materials. In this manner, diagnostic testing and treatment of, for example, the lungs of the patient, can be performed.

However, the handling of radioactive materials can be dangerous. Therefore, an apparatus is known from U.S. Pat. No. 4,510,929, the entire disclosure of which is incorporated herein by reference, which provides for such diagnostic testing using radioactive materials. Such apparatus is portable, adequately shields the hospital staff from radioactive exposure, and is disposable. Generally, the radioactive material is mixed with incoming oxygen in a nebulizer so as to become aerosolized with the aid of an orifice-diffuser arrangement. Then, the patient breathes through a first tube which is connected with the nebulizer so that minute particles of the radioactive material are supplied to the patient's lungs.

The arrangement of this apparatus, however, is somewhat complex. In the first place, it requires separate conduits for inhale and exhale, with a valve situated in each conduit, and with a third conduit interconnecting the inhale and exhale conduits. The valves are necessary to prevent any exhale through the inhale conduit, and to prevent any inhale through the exhale conduit. Further, the exhale conduit is connected to a filter, the latter positioned in a common housing adjacent the nebulizer. The outlet of the filter is in the closed housing and, in this regard, the housing has an approximate volume of three liters. Because of this arrangement of the filter and nebulizer, the apparatus becomes relatively bulky.

Still further, the parts of the nebulizer are separately constructed, thereby rendering the structure complex and the assembly thereof time-consuming, thus increasing the cost of the apparatus. In addition, because of the arrangement in this apparatus, if there is a short interruption in the supply of oxygen or radioactive material, or if supplies of the same are sporadic, there may not be an even distribution of the radioactive material with the oxygen. Also, the arrangement of the diffuser may not satisfactorily break up the radioactive particles.

OBJECTS AND SUMMARY OF THE INVENTION

Accordingly, it is an object of the present invention to provide a disposable radioactive inhalation apparatus that avoids the aforementioned difficulties encountered in the prior art.

It is another object of the present invention to provide an extremely compact disposable radioactive aerosol inhalation apparatus.

It is still another object of the present invention to provide a disposable radioactive aerosol inhalation apparatus that connects the filter and nebulizer in line by means of a single connecting conduit, with the outlet of the filter in fluid communication with ambient atmosphere and a single conduit for inhale and exhale connected to the single connecting conduit interconnecting the filter and nebulizer.

It is still another object of the present invention to provide a disposable radioactive aerosol inhalation apparatus that provides prolonged contact, and thereby greater intimate mixing, of the radioactive material and oxygen.

It is yet another object of the present invention to provide a disposable radioactive aerosol inhalation apparatus in which the oxygen and radioactive solution first enter into a chamber where intimate mixing occurs to form airborne particles, and then the airborne particles of radioactive material and the oxygen exit through a small orifice, so as to ensure satisfactory mixing with an even distribution.

It is a further object of the present invention to provide a disposable radioactive aerosol inhalation apparatus that positions the diffuser immediately above the small orifice through which the airborne radioactive particles emerge, to ensure satisfactory diffusion of a greater amount of such particles and to prevent reforming of the same.

It is a still further object of the present invention to provide a disposable radioactive aerosol inhalation apparatus in which the oxygen supply tube, the radioactive solution supply tube, the mixing chamber, the small exit orifice and the diffuser are made from a single piece of molded plastic.

In accordance with an aspect of the present invention, aerosol inhalation apparatus for supplying an aerosol mist containing radioactive tagged particles and air to a person, includes nebulizer means for producing the aerosol mist containing radioactive tagged particles and air, the nebulizer means including mixing chamber means for mixing the radioactive tagged particles and air to form the aerosol mist; filter means for filtering air traveling therethrough, the filter means having a first end open to ambient atmosphere and a second end; a first conduit connecting the filter means and the nebulizer means; a second conduit having a first end fluidly connected to the first conduit, and a second end; a mouthpiece connected to the second end of the second conduit; and a reusable container for containing the nebulizer means, filter means and first conduit; whereby the aerosol mist travels to the second conduit from the nebulizer means and the first conduit when the person inhales, and exhaust air and aerosol mist travel to the filter means from the second conduit through the first conduit when the person exhales such that the exhaust air is expelled to ambient atmosphere and the aerosol mist is trapped by the filter means.

In accordance with another aspect of the present invention, aerosol inhalation apparatus for supplying an aerosol mist containing radioactive tagged particles and air to a person, includes (a) nebulizer means for producing the aerosol mist containing radioactive tagged particles and air, the nebulizer means including
 (1) a housing for containing radioactive solution;
 (2) aerosol means in the housing for producing the aerosol mist, the aerosol means including
  (A) mixing chamber means for mixing the radioactive tagged particles and air to form the aerosol mist, the mixing chamber means having a small outlet opening;
  (B) oxygen supply means for supplying oxygen to the mixing chamber means;

(C) radioactive solution supply means for supplying the radioactive solution from the housing to the mixing chamber means in response to the supply of oxygen thereto, whereby the aerosol mist exits through the small outlet opening;

(3) diffuser means positioned immediately above the small outlet opening for breaking up radioactive tagged particles of the aerosol mist into smaller radioactive tagged particles;

(b) filter means for filtering air traveling therethrough, the filter means having a first end open to ambient atmosphere and a second end;

(c) a first conduit connecting the filter means and the nebulizer means;

(d) a second conduit having a first end fluidly connected to the first conduit, and a second end;

(e) a mouthpiece connected to the second end of the second conduit; and (f) a reusable container for containing the nebulizer means, filter means and first conduit;

(g) whereby the aerosol mist travels to the second conduit from the nebulizer means and the first conduit when the person inhales, and exhaust air and aerosol mist travel to the filter means from the second conduit through the first conduit when the person exhales such that the exhaust air is expelled to ambient atmosphere and the aerosol mist is trapped by the filter means.

The above and other objects, features and advantages of the present invention will become readily apparent from the following detailed description which is to be read in connection with the accompanying drawings.

BRIEF DESCRIPTION OF THE DRAWINGS

FIG. 1 is a perspective view of a disposable radioactive aerosol inhalation apparatus according to the present invention, in disassembled condition;

FIG. 2 is a perspective view of the disposable radioactive aerosol inhalation apparatus of FIG. 1, in assembled condition and showing the addition of radioactive solution thereto;

FIG. 3 is a perspective view of the disposable radioactive aerosol inhalation apparatus of FIG. 2, being assembled on an IV support stand;

FIG. 4 is a side elevational view of the disposable radioactive aerosol inhalation apparatus of FIG. 3 in use;

FIG. 7 is cross-sectional view of the disposable radioactive aerosol inhalation apparatus of FIG. 5, taken along line 7—7 thereof;

FIG. 8 is cross-sectional view of the disposable radioactive aerosol inhalation apparatus of FIG. 4, taken along line 8—8 thereof; and FIG. 9 is a perspective view of the aerosol device of the nebulizer of the disposable radioactive aerosol inhalation apparatus of FIG. 4.

DETAILED DESCRIPTION OF A PREFERRED EMBODIMENT

Figure 5:
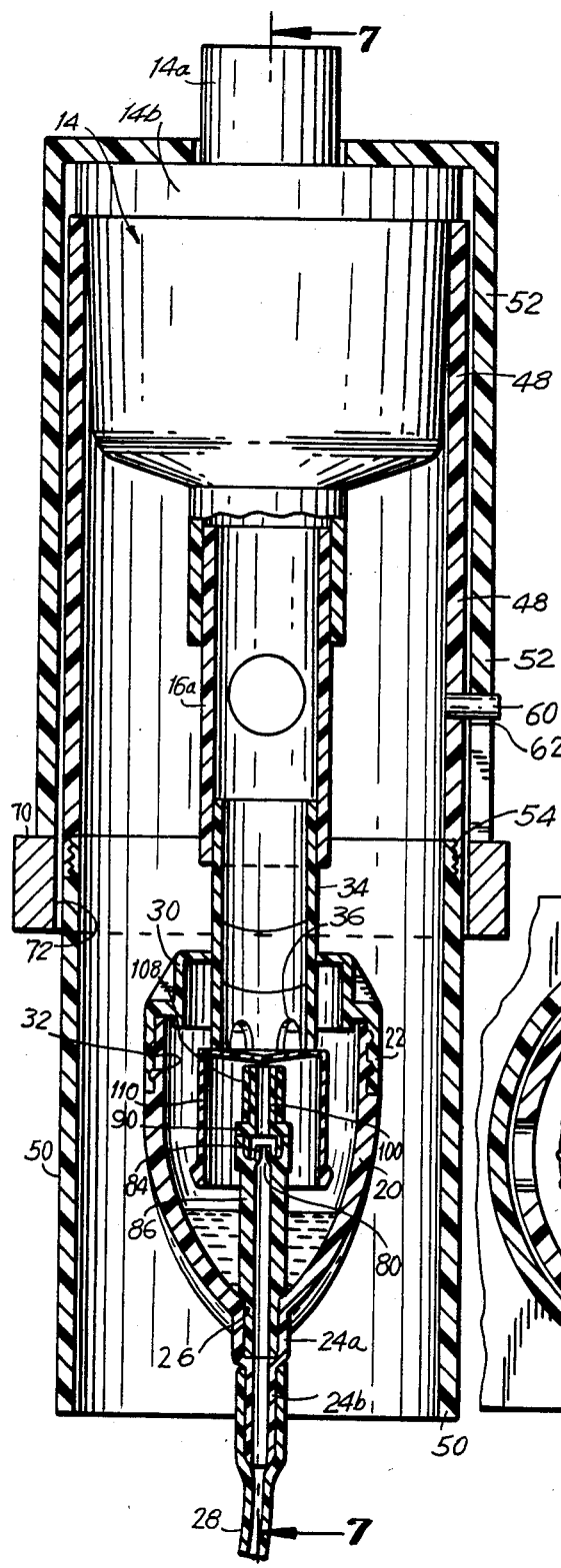
FIG. 5 is cross-sectional view of the disposable radioactive aerosol inhalation apparatus of FIG. 4, taken along line 5—5 thereof.
Figure 6:
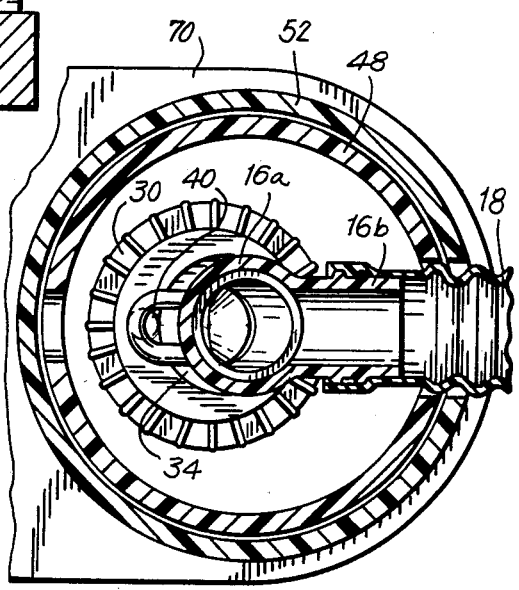
FIG. 6 is cross-sectional view of the disposable radioactive aerosol inhalation apparatus of FIG. 4, taken along line 6—6 thereof.

Referring to the drawings in detail, and initially to FIGS. 5 and 7 thereof, a disposable radioactive aerosol inhalation apparatus 10 according to the present invention generally includes a nebulizer 12 for producing an aerosol mist containing radioactive tagged particles and air, a filter 14 having an outlet in fluid communication with ambient atmosphere, a first conduit 16 interconnecting nebulizer 12 and filter 14, and a second conduit 18 connected with first conduit 16 and through which the person inhales and exhales.

Nebulizer 12 includes a bowl-shaped housing 20 formed with external screw threads 22 at the upper end thereof. Housing 20 is also integrally formed with an oxygen inlet pipe 24 at the lower end thereof which starts at an opening 26 in housing 20 and extends downwardly therefrom. As shown, oxygen inlet pipe 24 tapers down from a large diameter secton 24a to a small diameter section 24b, thereby forming an annular shoulder 24c positioned within pipe 24. Preferably, housing 20, including pipe 24, is made of a relatively rigid plastic material. A flexible hose 28 is stretched over small diameter section 24b of pipe 24, and is connected with a pressurized source of oxygen, for supplying oxygen to housing 20, for reasons which will be described in greater detail hereinafter. Oxygen is preferably supplied at the rate of 8-12 liters/minute.

Nebulizer 12 further includes a cover 30 for housing 20. Cover 30 is provided with internal screw threads 32 which screw-threadedly receive screw threads 22 of housing 20 in a mating relation. Cover 30 is also provided with a centrally located outlet tube 34 which extendspartially above and partially below cover 30, outlet tube 34 being cut away at its lower end to define circumferentially spaced, arcuate openings 36. Preferably, cover 30, including outlet pipe 34, is made of a relatively rigid plastic material. In addition, cover 30 has an opening 38 formed therein, which is covered by a puncturable, self-sealing sealing membrane 40 through which a needle 42 (FIG. 2) can be inserted for supplying the radioactive solution to housing 20. Preferably, the solution will be technetium TC99m DTPA solution.

First conduit 16 includes a vertically, oriented connecting pipe 16a that connects the upper end of outlet pipe 34 to the lower end of filter 14, and the opposite outlet end 14a of filter 14 is in fluid communication with ambient atmosphere. A central horizontal pipe 16b is formed integrally with connecting pipe 16a, and is connected with second conduit 18 at a junction opening of central horizontal pipe 16b. The opposite end of second conduit 18 has a mouthpiece 44 (FIGS. 1, 3 and 4) attached thereto through which the patient can breathe. Preferably, first conduit 16 is made of a relatively rigid plastic material, while second conduit 18 is made of a softer plastic material in a bellows type arrangement which permits flexibility so as to accommodate each patient.

As shown in FIGS. 1–5 and 7, the above arrangement is housed in a shielded canister 46 which is comprised of three cylindrical containers 48, 50 and 52. Cylindrical container 48 is connected in line with cylindrical container 50 by a screw threaded securement 54, and forms the main shielded container of the canister. Both containers 48 and 50 preferably have the same outside diameter. Cylindrical container 48 is formed with a vertically oriented slot 56 extending from the upper end thereof and terminating short of the lower end thereof. In addition, cylindrical container 48 is formed with a shorter elongated slot 58 near the lower end thereof and diametrically opposite slot 56, as shown in FIG. 7. A projection pin 60 is formed 90 degrees out of phase with slots 56 and 58 on the external surface of cylindrical container 48 and near the lower end thereof.

When cylindrical containers 48 and 50 are assembled in screw threaded relation, the assembly of nebulizer 12, filter 14, first conduit 16 and second conduit 18, is inserted within containers 48 and 50, as shown in FIG. 1, with second conduit 18 sliding within slot 56 of first container 48. The upper end of filter 14 is formed with a large diameter circumferential lip 14b which rests upon the open upper end of container 48, nd which thereby supports the assembly of nebulizer 12, filter 14, first conduit 16 and second conduit 18, within containers 48 and 50, as shown in FIG. 7.

Cylindrical container 52 is formed of a larger diameter than container 48 and is intended to fit thereover. In order to secure container 52 to container 48, container 52 includes a key slot 62 at the lower end thereof which fits over projection pin 60 when container 52 is slipped over container 48. When container 52 is slipped over container 48 and twisted relative thereto, the mating of projection pin 60 and key slot 62 prevent the accidental removal of container 52. In addition, a similar key slot 64 is formed 90 degrees out of phase with key slot 62 at the lower end of container 52 for receiving second conduit 18 when container 52 is assembled with container 48. Still further, an elongated slot 66 is formed diametrically opposite key slot 64, so as to be in alignment with slot 58 of container 48 when container 52 is in assembled position with container 48, and thereby form an opening 68, as shown in FIG. 2. Opening 68 is provided to permit access for needle 42 to supply the radioactive solution to housing 20 through membrane 40.

With apparatus 10 assembled as shown in FIG. 2, apparatus 10 can be supported in an IV support stand 70, as shown in FIGS. 3, 5 and 7, whereby only container 50 fits within an aperture 72 of IV support stand 70, and the lower end of container 52 thereby supports apparatus 10. It will be appreciated that, with the arrangement thus far described, apparatus 10 is extremely compact, because filter 14 and nebulizer 12 are connected in line with a single conduit 16, with the outlet end 14a of filter 14 in fluid communication with ambient atmosphere and a single conduit 18 for inhale and exhale connected to the single conduit 16 interconnecting filter 14 and nebulizer 12.

Referring now to FIGS. 5-9, with particular attention to FIG. 9, nebulizer 12 includes an aerosol device 74 which breaks up the radioactive solution into small particles, for example, under 0.5 microns in size, and supplies the same in an airborne state to first conduit 16. Aerosol device 74 cn be made from a soft plastic material.

Specifically, aerosol device 74 includes a housing 76 which defines a chamber 78 that is open at the upper end thereof in its unassembled state, as shown in FIG. 9. Housing 76 and chamber 78 preferably have an oblong configuration, as shown, although the present invention is not so limited. The lower wall 76a (FIG. 7) of housing 76 that defines chamber 78 is formed with two spaced openings 80 and 82, with a reduced diameter nozzle 84 extending upwardly from and in fluid communication with opening 80.

An oxygen supply tube 86 is connected to the bottom of lower wall 76a in fluid communication with opening 80, and thereby, with nozzle 84. Oxygen supply tube 86 has a large diameter section 86a connected with lower wall 76a and a small diameter section 86b at the free end thereof, thereby defining a shoulder 86c therebetween. A radioactive solution supply tube 88 is connected to the bottom of lower wall 76a in fluid communication with opening 82. When aerosol device 74 is positioned within housing 20, as shown, small diameter section 86b of oxygen supply tube 86 fits snugly within large diameter section 24a of oxygen inlet pipe 24, with soulder 86c providing a limit on the extent of travel therein. In this manner, aerosol device 74 is supported within housing 20. In this position, the lower, open, free end of radioactive solution supply tube 88 is positioned immediately above the bottom of housing 20 with a small clearance therebetween, for receiving the radioactive solution in housing 20.

Aerosol device 74 further includes a cover 90 pivoted on housing 76 by means of a living hinge 92. A sealing device 94, in the form of an oblong wall having outer dimensions similar to the inner dimensions which define chamber 78, is secured to the underside of cover 90. Thus, when cover 90 is closed to the position shown in FIGS. 5 and 7, sealing device 94 fits snugly against the inner walls of housing 76 that defines chamber 78, thereby closing chamber 78. In this position, a small opening 96 in cover 90 is located near nozzle 84. With the arrangement thus far described, oxygen is supplied under pressure, for example, at the rate of 8-12 liters/minute, through oxygen supply tube 86 to chamber 78. This, in turn, sucks radioactive solution from housing 20, up radioactive solution supply tube 88, to chamber 78, where the two are intemately mixed. As a result, the radioactive solution is rendered airborne with the supplied oxygen, and the airborne particles exit through opening 96.

Aerosol device 74 further includes a diffuser 98 in the form of a convex shaped bowl which is positioned immediately above small opening 96, with a small clearance therebetween. When the airborne radioactive particles exit opening 96, they impinge upon diffuser 98, which breaks up the particles into smaller particles, generally under 0.5 microns in size.

In accordance with the present invention, diffuser 98 is formed integrally with cover 90, housing 76, oxygen supply tube 86 and radioactive solution supply tube 88. Specifically, a post 100 is formed on top of cover 90 and a flange 102 extends outwardly therefrom. A diffuser support 104 is attached to flange 102 by a living hinge 106, and diffuser support 104 includes a U-shaped clasp 108 having one leg thereof attached to diffuser support 104. Diffuser 98 is connected to U-shaped clasp 108. When diffuser support 104 is pivoted about living hinge 106, U-shaped clasp 108 is wrapped about post 100 in a tight manner to securely, but removably, position diffuser 98 immediately above small opening 96.

In addition, a cylindrical cap 110 which is open at its lower end, is positioned over post 100, diffuser 98, cover 90, housing 76, and partially over tubes 86 and 88.

In operation, oxygen is supplied through oxygen supply tube 86. This, in turn, sucks radioactive solution through radioactive solution supply tube 88, into chamber 78 so as to intimately mix the same with the oxygen. Because of such mixing in a substantially closed chamber, there is very even distribution of the radioactive solution particles with the oxygen. As a result, airborne particles of radioactive solution exit from small opening 96 and impinge on diffuser 98 which breaks up the airborne particles into small airborne particles.

The small airborne particles travel around the underside of cap 110 and enter outlet tube 34 through openings 36 thereof. Larger airborne particles merely fall back into the reservoir of radioactive solution at the bottom of housing 20. At this time, the patient has also begun breating through mouthpiece 44. As the patient inhales, the airborne radioactive particles from outlet tube 34 enter mouthpiece 44 through first conduit 16 and second conduit 18. In addition, ambient air is sucked in through filter 14, first conduit 16 and second conduit 18. When the patient exhales, the exhaust air and radioactive matter exit through second conduit 18 and first conduit 16 to filter 14, where the radioactive exhaust matter is trapped. The air, however, is released into the atmosphere.

Thus, with the present invention, there is prolonged contact, and thereby greater intimate mixing, of the radioactive material and oxygen, in chamber 78. As a result, when the airborne particles of radioactive material and oxygen exit through small opening 96, satisfactory mixing with an even distribution is ensured. Still further, by positioning the diffuser immediately above small opening 96 through which the airborne radioactive particles emerge, satisfactory diffusion of a greater amount of such particles is ensured along with the prevention of substantial reforming of the same.

The present invention also provides for an economy in construction and costs by manufacturing the oxygen nozzle, radioactive solution nozzle, intermediate chamber, small orifice thereof and diffusion from a single piece of molded plastic.

Having described a specific preferred embodiment of the invention with reference to the accompanying drawings, it will be appreciated that the present invention is not limited to that precise embodiment, and that various changes and modifications can be effected therein by one of ordinary skill in the art without departing from the spirit or scope of the invention as defined in the appended claims.

What is claimed is:

1. An aerosol inhalation apparatus for supplying an aerosol mist containing radioactive tagged particles and air to a person, comprising:
    nebulizer means for producing said aerosol mist containing radioactive tagged particles and air, said nebulizer means including mixing chamber means for mixing said radioactive tagged particles and air to form said aerosol mist;
    filter means for filtering air traveling therethrough in opposite directions, said filter means having a first end open to ambient atmosphere and a second end;
    first conduit means, connecting said filter means and said nebulizer means, for supplying an aerosol mist from said nebulizer means and air from the ambient atmosphere from said filter means to a junction opening of said first conduit means during an inhalation operation and for supplying exhaust air and aerosol mist from said junction opening to said filter means during an exhalation operation, said junction opening being situated between said filter means and said nebulizer means;
    second conduit means for supplying the aerosol mist and air to the person from said junction opening during the inhalation operation and for supplying exhaust air and aerosol mist to said junction opening during the exhalation operation, said second conduit means having a first end fluidly connected to said junction opening of said first conduit means, and a second end; and
    a mouthpiece connected to the second end of said second conduit means;
    whereby said aerosol mist travels to said second conduit means from said nebulizer means and said first conduit means and ambient atmosphere travels to said second conduit means from said filter means and said first conduit means when the person inhales, and exhaust air and aerosol mist travel to said filter means from said second conduit means through said first conduit means when the person exhales such that said exhaust air is expelled to ambient atmosphere and said aerosol mist is trapped by said filter means.

2. Apparatus according to claim 1; wherein said nebulizer means and filter means are connected substantially in line with each other.

3. Apparatus according to claim 1; wherein said filter means is always in fluid communication with said nebulizer means through said first conduit means.

4. Apparatus according to claim 1; wherein said nebulizer means includes:
    (a) a housing for containing radioactive solution;
    (b) aerosol means in said housing for producing said aerosol mist, said aerosol means including:
        (1) said mixing chamber means having a small outlet opening,
        (2) oxygen supply means for supplying oxygen to said mixing chamber means,
        (3) radioactive solution supply means for supplying said radioactive solution from said housing to said mixing chamber means in response to the supply of oxygen thereto, whereby said aerosol mist exits through said small outlet opening; and
    (c) diffuser means positioned immediately above said small outlet opening for breaking up radioactive tagged particles of said aerosol mist into smaller radioactive tagged particles.

5. Apparatus according to claim 4; wherein said housing includes an outlet pipe connected with said first conduit means, and said nebulizer means further includes cap means in said housing in surrounding relation to said diffuser means, said small outlet opening and an upper portion of said aerosol means, said cap means being open at a lower end thereof to permit egress of said aerosol mist from said small outlet opening to said first conduit means.

6. Apparatus according to claim 4; wherein walls defining said mixing chamber means said oxygen supply means, said radioactive solution supply means and said diffuser means are integrally formed as a unitary molded unit.

7. Apparatus according to claim 4; wherein said aerosol means includes a support adjacent said mixing chamber means and a cover hingedly attached to said support for closing and sealing said mixing chamber means.

8. Apparatus according to claim 7; wherein said diffuser means is connected to said cover by means of a hinge arrangement.

9. Apparatus according to claim 8; wherein said aerosol means includes a post connected to said cover, a flange connected to said post, a diffuser support hingedly connected to said flange by said hinge arrangement, a clasp secured to said diffuser support for releasable securement to said post, and said diffuser means connected to said diffuser support such that said diffuser means is positioned immediately above said small outlet opening when said clasp is pivoted about said hinge arrangement in securement with said post.

10. Apparatus according to claim 4; wherein said diffuser means includes convex-shaped bowl means facing said small outlet opening.

11. An aerosol inhalation apparatus for supplying an aerosol mist containing radioactive tagged particles and air to a person, comprising:
(a) nebulizer means for producing said aerosol mist containing radioactive tagged particles and air, said nebulizer means including:
 (1) a housing for containing radioactive solution;
 (2) aerosol means in said housing for producing said aerosol mist, said aerosol means including:
  (A) mixing chamber means for mixing said radioactive tagged particles and air to form said aerosol mist, said mixing chamber means having a small outlet opening;
  (B) oxygen supply means for supplying oxygen to said mixing chamber means;
  (C) radioactive solution supply means for supplying said radioactive solution from said housing to said mixing chamber means in response to the supply of oxygen thereto, whereby said aerosol mist exits through said small outlet opening;
 (3) diffuser means positioned immediately above said small outlet opening for breaking up radioactive tagged particles of said aerosol mist into smaller radioactive tagged particles;

(b) filter means for filtering air traveling therethrough in opposite directions, said filter means having a first end open to ambient atmosphere and a second end;

(c) first conduit means, connecting said filter means and said nebulizer means, for supplying an aerosol mist from said nebulizer means and air from the ambient atmosphere from said filter means to a junction opening of said first conduit means during an inhalation operation and for supplying exhaust air and aerosol mist from said junction opening to said filter means during an exhalation operation, said junction opening being situated between said filter means and said nebulizer means;

(d) second conduit means for supplying the aerosol mist and air tothe person from said junction opening during the inhalation operation and for supplying exhaust air and aerosol mist to said junction opening during the exhalation operation, said second conduit means having a first end fluidly connected to said junction opening of said first conduit means, and a second end; and (e) a mouthpiece connected to the second end of said second conduit means;

(f) whereby said aerosol mist travels to said second conduit means from said nebulizer means and said first conduit means and ambient atmosphere travels to said second conduit means from said filter means and said first conduit means when the person inhales, and exhaust air and aerosol mist travel to said filter means from said second conduit means through said first conduit means when the person exhales such that said exhaust air is expelled to ambient atmosphere and said aerosol mist is trapped by said filter means.

* * * * *